(12) United States Patent
Lee et al.

(10) Patent No.: US 10,533,961 B2
(45) Date of Patent: Jan. 14, 2020

(54) METHOD AND SYSTEM FOR NON-DESTRUCTIVE METROLOGY OF THIN LAYERS

(71) Applicant: Nova Measuring Instruments, Inc., Santa Clara, CA (US)

(72) Inventors: Wei Ti Lee, San Jose, CA (US); Heath Pois, Fremont, CA (US); Mark Klare, Poughkeepsie, NY (US); Cornel Bozdog, San Jose, CA (US)

(73) Assignee: NOVA MEASURING INSTRUMENTS, INC., Santa Clara, CA (US)

( * ) Notice: Subject to any disclaimer, the term of this patent is extended or adjusted under 35 U.S.C. 154(b) by 0 days.

(21) Appl. No.: 15/773,145

(22) PCT Filed: Nov. 2, 2016

(86) PCT No.: PCT/US2016/060147
§ 371 (c)(1),
(2) Date: May 2, 2018

(87) PCT Pub. No.: WO2017/079322
PCT Pub. Date: May 11, 2017

(65) Prior Publication Data
US 2018/0328871 A1    Nov. 15, 2018

Related U.S. Application Data

(60) Provisional application No. 62/249,845, filed on Nov. 2, 2015.

(51) Int. Cl.
*G01N 23/227* (2018.01)
*G01N 23/223* (2006.01)
(Continued)

(52) U.S. Cl.
CPC ......... *G01N 23/2273* (2013.01); *G01B 11/06* (2013.01); *G01B 15/02* (2013.01);
(Continued)

(58) Field of Classification Search
CPC .......... G01N 23/2273; G01N 23/2208; G01N 23/223; G01N 2223/305; G01N 2223/61; G01N 2223/633; G01B 15/02
See application file for complete search history.

(56) References Cited

U.S. PATENT DOCUMENTS 6,041,096 A *  3/2000  Doi ..................... G01N 23/223
378/45
8,774,359 B1 *  7/2014  Zhuang ............. G01N 23/2273
378/70
(Continued)

*Primary Examiner* — Nicole M Ippolito
*Assistant Examiner* — Sean M Luck
(74) *Attorney, Agent, or Firm* — Womble Bond Dickinson (US) LLP; Joseph Bach, Esq.

(57) ABSTRACT

Determining a property of a layer of an integrated circuit (IC), the layer being formed over an underlayer, is implemented by performing the steps of: irradiating the IC to thereby eject electrons from the IC; collecting electrons emitted from the IC and determining the kinetic energy of the emitted electrons to thereby calculate emission intensity of electrons emitted from the layer and electrons emitted from the underlayer calculating a ratio of the emission intensity of electrons emitted from the layer and electrons emitted from the underlayer; and using the ratio to determine material composition or thickness of the layer. The steps of irradiating IC and collecting electrons may be performed using x-ray photoelectron spectroscopy (XPS) or x-ray fluorescence spectroscopy (XRF).

18 Claims, 6 Drawing Sheets

(51) Int. Cl.
  *G01N 23/22* (2018.01)
  *G01N 23/2273* (2018.01)
  *G01B 11/06* (2006.01)
  *G01B 15/02* (2006.01)
  *G01N 23/2208* (2018.01)

(52) U.S. Cl.
  CPC ....... *G01N 23/223* (2013.01); *G01N 23/2208* (2013.01); *G01N 2223/305* (2013.01); *G01N 2223/61* (2013.01); *G01N 2223/633* (2013.01)

(56) References Cited

U.S. PATENT DOCUMENTS

| | | | |
|---|---|---|---|
| 2006/0243904 A1* | 11/2006 | Schueler | G01B 15/02 250/305 |
| 2011/0210246 A1* | 9/2011 | Cohen | G01N 23/2273 250/305 |
| 2015/0032398 A1* | 1/2015 | Peterlinz | G01N 23/2206 702/81 |
| 2015/0198435 A1* | 7/2015 | Vaid | H01L 22/12 438/16 |
| 2015/0308969 A1* | 10/2015 | Pois | G01B 15/02 378/46 |

* cited by examiner

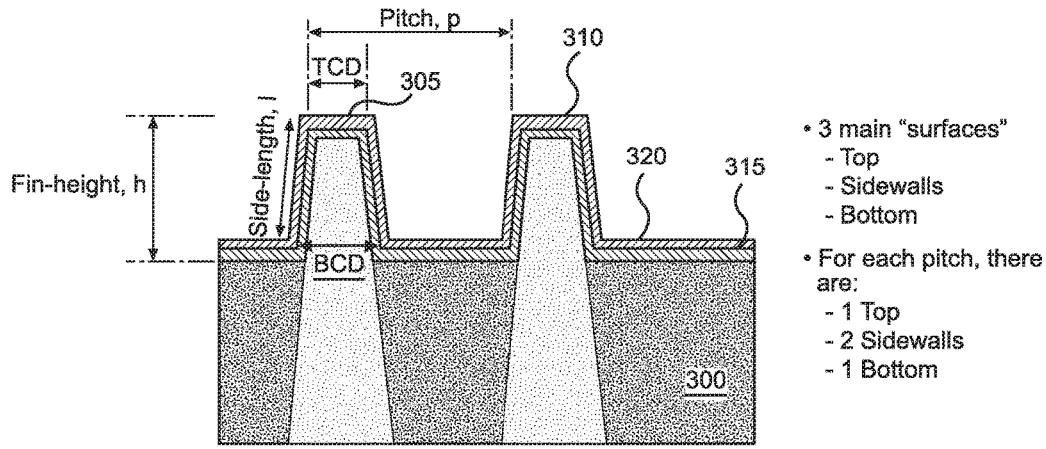

Intensity Of SpeciesA: $I_{FinStructre,A} = I_{A,Top} + 2I_{A,Sidewall} + I_{A,Bottom}$

FIG. 3

Full Equations for Hf, Si-O and Si $$I_{Hf} = \frac{1}{K_{Hf} G_{Top}} \left[ 1 - e^{\frac{-t_{HfO2}}{\lambda_{Hf,HfO2}}} \right]$$

$$+ \frac{2}{K_{Hf} * G_{Sidewall}} \left( \left[ 1 - e^{\frac{-t_{HfO2}}{\lambda_{Hf,HfO2}}} \right] + \left[ 1 - e^{\frac{-t_{HfO2}}{\lambda_{Hf,HfO2}}} \right] e^{\frac{-2t_{SiO2}}{\lambda_{Hf,SiO2}}} e^{\frac{-TCD_{fin}}{\lambda_{Hf,Si}}} e^{\frac{-t_{HfO2}}{\lambda_{Hf,HfO2}}} \right)$$

$$+ \frac{1}{K_{Hf} * G_{Bottom}} \left[ 1 - e^{\frac{-t_{HfO2}}{\lambda_{Hf,HfO2}}} \right]$$

$$I_{Si-O} = \frac{1}{K_{Si-O} G_{Top}} \left[ 1 - e^{\frac{-t_{SiO2}}{\lambda_{Si-O,SiO2}}} \right] e^{\frac{-t_{HfO2}}{\lambda_{Si-O,HfO2}}}$$

$$+ \frac{2}{K_{Si-O} * G_{Sidewall}} \left( \left[ 1 - e^{\frac{-t_{SiO2}}{\lambda_{Si-O,SiO2}}} \right] e^{\frac{-t_{HfO2}}{\lambda_{Si-O,HfO2}}} + \left[ 1 - e^{\frac{-t_{SiO2}}{\lambda_{Si-O,SiO2}}} \right] e^{\frac{-t_{SiO2}}{\lambda_{Si-O,SiO2}}} e^{\frac{-TCD_{fin}}{\lambda_{Si-O,Si}}} e^{\frac{-t_{HfO2}}{\lambda_{Si-O,HfO2}}} \right)$$

$$+ \frac{1}{K_{Si-O} * G_{Bottom}} e^{\frac{-t_{HfO2}}{\lambda_{Si-O,HfO2}}}$$

$$I_{Si} = \frac{1}{K_{Si} G_{Top}} e^{\frac{-t_{SiO2}}{\lambda_{Si,SiO2}}} e^{\frac{-t_{HfO2}}{\lambda_{Si,HfO2}}} + \frac{2}{K_{Si} * G_{Sidewall}(w,h,p)} \left[ 1 - e^{\frac{-w_{fin}}{\lambda_{Si,Si}}} \right] e^{\frac{-t_{SiO2}}{\lambda_{Si,SiO2}}} e^{\frac{-t_{HfO2}}{\lambda_{Si,HfO2}}}$$

FIG. 4A

Where: $G_{Tov} = \dfrac{P}{TCD}$ $G_{Sidewall} = \dfrac{ap}{\sqrt{h^2 + \left(\dfrac{(BCD-TCD)}{2}\right)^2}}$ $G_{Bottom} = \dfrac{bp}{p - BCD}$ Constraints:

$TCD \leq BCD < P$ w, p and h can be fed from OCD
Since aspect ratio is relatively low, b~1
Therefore, in the simplest case, the only additional parameter is a.

FIG. 4B

Where: $G_{Tov} = \dfrac{cp}{TCD + t_{sidewall}}$ $G_{Sidewall} = \dfrac{ap}{\sqrt{h^2 + \left(\dfrac{(BCD-TCD)}{2}\right)^2}}$ $G_{Bottom} = \dfrac{bp}{p - BCD - d * (t_{IL} - t_{HK})}$ Constraints:

$TCD \leq BCD < P$

FIG. 4C

METHOD AND SYSTEM FOR NON-DESTRUCTIVE METROLOGY OF THIN LAYERS

RELATED APPLICATION

This Application claims priority benefit from U.S. Provisional Application Ser. No. 62/249,845, filed on Nov. 2, 2015, the disclosure of which is incorporated herein by reference in its entirety.

FIELD OF THE INVENTION

The invention generally relates to techniques for examining microelectronic structures and specifically to techniques for measuring layer thickness and composition on structures using photoelectron spectroscopy and x-ray fluorescence.

BACKGROUND

Integrated circuits typically comprise a number of layers formed on a silicon substrate. As integrated circuits become smaller, and the thickness of layers comprising the integrated circuits is reduced, the behavior of devices formed from these layers often depends on the thickness or composition of a specific layer. For example, a transistor formed on a silicon substrate may have different characteristics depending on the thickness or composition of the gate of the transistor. It may therefore be useful to determine a thickness and composition of a layer in a microelectronic device such as an integrated circuit.

The thickness or composition of a layer in a microelectronic device such as an integrated circuit may be determined using one of several techniques. The microelectronic device typically includes a structure including several layers built up over a substrate. Techniques that may be used to determine a thickness and/or composition of a specific layer in a structure include ellipsometry, using an electron probe with wavelength dispersive spectrometer(s), angle-resolved x-ray photoelectron spectroscopy (XPS), and secondary ion mass spectrometry (SIMS).

Angle-resolved XPS uses photoelectron spectroscopy to determine a thickness and/or composition of a layer or multiple layers. Photoelectron spectroscopy bombards a sample with photons having a specific wavelength (here, x-ray photons), which excite the atoms of the sample to generate a photoelectron having a characteristic energy for the sample. The technique depends on measuring photoelectrons at different emission angles from the sample surface, for example by tilting the sample with respect to an electron energy analyzer.

As technologies advance, improved methods for determining thickness and compositions of thin layers are needed.

SUMMARY

The following summary of the invention is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

Various discloses embodiments provide methods and systems for investigating semiconductor integrated circuits. The disclosed embodiments are especially suitable for investigating thin layers formed during the production of the IC. The embodiments enable investigating characteristics such as composition and thickness of thin films layered over a substrate. The embodiments make use of a photoelectric effect to calculate emission intensities for various elements from each layer to determine composition and thickness of the layers. A ratio calculation enhances the thickness determination and may be performed as iterative process to improve on the thickness determination.

Disclosed embodiments also incorporate exterior measurements to enhance the thickness determination. For example, some embodiments utilize measurements of optical critical dimension (OCD) tool to enhance the thickness calculations. In specific examples, the OCD measurements are used to develop coefficients that are used to improve the thickness determination, especially when the surface of the device has a non-flat topology. The use of the coefficients is especially effective when the device includes features that repeat in a consistent order.

According to aspects of the invention, a method for determining a property of a layer of an integrated circuit (IC) is provided, comprising the steps of: placing the IC on a test surface; obtaining topographical data of a top surface of the IC; irradiating the top surface of the IC; collecting radiation intensity emanating from the top surface of the IC and generating measured intensity signal; calibrating the measured intensity signal using the topographical data to obtained calibrated radiation intensity; and using the calibrated radiation intensity to determine the property of the layer. The properties investigated may include elemental composition and thickness. The method may operate on flat layers or structured layers with peaks and valleys, generally referred to herein as fins. The structures of the fins may be investigated beforehand either by using a CAD design data for the IC, or using measurement devices such as CD-SEM, OCD, etc. The process of obtaining topographical data may be performed by one of: interrogating a stored CAD design data, measuring topographical features using electron beam, or measuring topographical features using optical illumination. This topographical data can be used to modify the model of flat layers to provide improved results.

According to further aspects, a method is provided for determining a property of a layer of an integrated circuit (IC), the layer being formed over an underlayer, comprising the steps of: irradiating the IC to thereby eject electrons from the IC; collecting electrons emitted from the IC and determining the kinetic energy of the emitted electrons to thereby calculate emission intensity of electrons emitted from the layer and electrons emitted from the underlayer; calculating a ratio of the emission intensity of electrons emitted from the layer and electrons emitted from the underlayer; and using the ratio to determine material composition or thickness of the layer. The steps of irradiating IC and collecting electrons may be performed using x-ray photoelectron spectroscopy (XPS) or x-ray fluorescence spectroscopy (XRF).

The intensity of electrons emitted from the layer may be calculated using the relationship:

$$I(X_i) = I_{infXi} * \left[1 - e^{\frac{-tx}{\lambda Xi(x)}}\right]$$

Where Xi is the photoelectron species from element X emitted from layer x, I(Xi) is intensity of the photoelectron signal, IinfXi is an intensity of a photoelectron signal emitted by a thick layer of x, tx is thickness of the layer, and $\lambda Xi(x)$ is electron attenuation length (EAL) of the photoelectron species (Xi) through the layer x.

The intensity of electrons emitted from the underlayer may be calculated using the relationship:

$$I(Y_i) = I_{infY_i} * e^{\frac{-tx}{\lambda Y_i(x)}}$$

Where $I(Y_i)$ is the intensity of a photoelectron signal comprising a photoelectron species $Y_i$ from the underlayer, tx is the thickness of the over-layer, and $\lambda Y_i(x)$ is the EAL of photoelectrons emitted by the species $Y_i$ in the layer.

The ratio may be calculated by using the relationship:

$$\frac{I(L)}{I(U)} = \frac{I_{infXi} * [1 - e^{\frac{-tL}{\lambda Xi(L)}}]}{I_{infY_i} * e^{\frac{-tL}{\lambda Y_i(L)}}}$$

wherein I(L) is measured intensity of photoelectrons emitted by the layer, while I(U) is measured intensity of photoelectrons emitted by the underlayer. I(infXi) and I(infYi) are measured intensities of a photoelectron emitted by a greater than 10 nm layer of Xi and Yi photoelectron species, respectively, $\lambda Xi(L)$ and $\lambda Yi(L)$ are electron attenuation lengths (EALs) of elements Xi and Yi photoelectrons through layer L.

In the more complicated case where there are two thin layers, the intensity of electrons emitted from the under layer may be calculated using the relationship:

$$I(Y_i) = I_{infY_i} * e^{\frac{-tx}{\lambda Y_i(x)}} * e^{\frac{-tz}{\lambda Y_i(z)}}$$

Where $I(Y_i)$ is the intensity of a photoelectron signal comprising a photoelectron species $Y_i$ from the substrate, tx is the thickness of the top-layer, tz is the thickness of the layer below, and $\lambda Y_i(x)$ $\lambda Y_i(z)$ are the EALs of photoelectrons of species $Y_i$ attenuated through the two layers of thickness tx and tz.

The ratio is then calculated by using the relationship:

$$\frac{I(L)}{I(U)} = \frac{I_{infXi} * [1 - e^{\frac{-tL}{\lambda Xi(L)}}]}{I_{infY_i} * e^{\frac{-tL}{\lambda Y_i(L)}} * e^{\frac{-tL-1}{\lambda Y_i(L-1)}}}$$

wherein I(L) is measured intensity of photoelectrons emitted by the layer, while I(U) is measured intensity of photoelectrons emitted by the underlayer. I(infXi) and I(infYi) again are measured intensities of a photoelectron emitted by a greater than 10 nm layer of Xi and Yi photoelectron species, respectively, $\lambda Xi(L)$ and $\lambda Yi(L)$, $\lambda Yi(L-1)$ are electron attenuation lengths (EALs) of elements Xi and Yi photoelectrons through layers L and U, the layer below L. Similar relationships can be develop for film stacks with more than two layers.

According to further aspects, a metrology module is provided for determining a property of a layer of an integrated circuit (IC), the module comprising: a first input port configured for receiving parameters corresponding to topography of a top surface of the IC; a second input port configured for receiving radiation intensity signal corresponding to radiation emission obtained from the top surface of the IC; a coefficient generator receiving the parameters and calculating at least one coefficient therefrom; a calibration module receiving the coefficient and using the coefficient to calibrate the radiation intensity signal to thereby produce a calibrated signal; a determination module receiving the calibration signal and using the calibration signal to generate a determination of the property of the layer. The emission radiation may indicate electron emission from the IC layers, so that the second input port may be coupled to a sensor of an x-ray photoelectron spectroscopy (XPS) or a sensor of an x-ray fluorescence spectroscopy (XRF). Also, the first input port may be coupled to an electron or OCD tool. The layer's property investigated may comprise at least one of thickness and chemical composition. The topography parameters may comprise at least one of: width of upper surface of a feature on the top surface of the IC, width of bottom surface of a feature on the top surface of the IC, height of a feature on the top surface of the IC, length or height of sidewall of a feature on the top surface of the IC, pitch of multiple features on the top surface of the IC. The coefficients may comprise a top coefficient correlated to the width of upper surface of a feature on the top surface of the IC, a sidewall coefficient correlated to length or height of sidewall of the feature on the top surface of the IC, and bottom coefficient correlated to width of bottom surface of the feature on the top surface of the IC. The top coefficient, the sidewall coefficient and the bottom coefficient may further correlate to a pitch of multiple features on the top surface of the IC.

According to yet further aspects, a system is provided for determining a thickness of a layer in a multi-layer structure, comprising: a critical dimension metrology tool; a thickness measurement metrology tool; and a thickness determining module; the thickness determining module comprising: a first input port coupled to the critical dimension metrology tool and configured for receiving from the critical dimension metrology tool parameters corresponding to topography of a top surface of the IC; a second input port configured for receiving radiation intensity signal from a sensor of the thickness measurement metrology tool, the radiation intensity signal corresponding to emission radiation detected by the sensor from the top surface of the IC; a coefficient generator receiving the parameters and calculating at least one coefficient therefrom; a calibration module receiving the coefficient and using the coefficient to calibrate the radiation intensity signal to thereby produce a calibrated signal; and a determination module receiving the calibration signal and using the calibration signal to generate a determination of the thickness of the layer.

Other aspects provide a machine readable medium having stored thereon executable program which, when executed, causes a machine to perform a method for determining a property of a layer, the method comprising: obtaining topographical data of a top surface of the IC; irradiating the top surface of the IC; collecting emission radiation intensity from the top surface of the IC and generating measured intensity signal; calibrating the measured intensity signal using the topographical data to obtained calibrated radiation intensity; and using the calibrated radiation intensity to determine the property of the layer.

Other aspects are disclosed by the detailed description with reference to the drawings.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

One or more embodiments of the present invention are illustrated by way of example and not limitation in the figures of the accompanying drawings, in which like references indicate similar elements and in which:

FIG. 3 illustrates two thin layers over a substrate having uneven topography;

FIG. 4A-4C illustrate generating coefficients to accommodate photon emission from uneven topography;

DETAILED DESCRIPTION

Figure 1A:
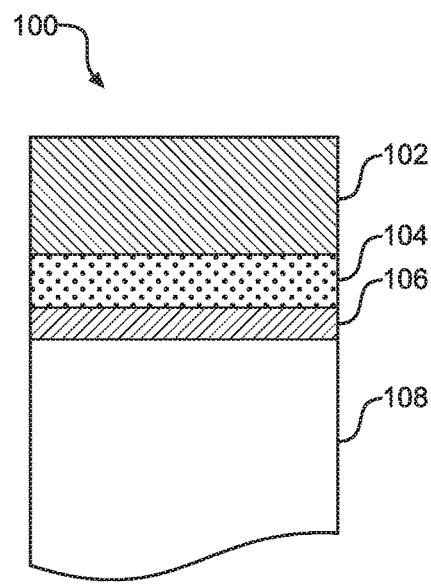
FIGS. 1A-1D illustrate two multi-layer structures and the intensities of different photoelectron signals emitted by the structures when subjected to photoelectron spectroscopy.

According to one embodiment of the invention, electron spectroscopy and/or x-ray fluorescence is used to determine the thickness and/or composition of one or more layers in a single or multi-layer structures on a substrate. The thickness may be determined by measuring the intensities of two electron/x-ray species emitted by the structures when bombarded with photons, electrons, etc. A predictive intensity function that is dependent on the thickness of a layer is determined for each electron/x-ray species. A ratio of two predictive intensity functions is formulated, and the ratio is iterated to determine the thickness of a layer of the structure. According to one embodiment, two (or more) electron/x-ray species may be measured from a single layer to determine a thickness and/or composition of that layer. According to another embodiment, two electron/x-ray species from different layers or from a substrate may be measured to determine a thickness and/or composition of the layer. Several techniques for determining the thickness and/or composition of different layers in different configurations are described below.

For measurements that are done over patterned areas, the intensity measurement is then "normalized" or "calibrated" using topographical information of the structures of the patterned area. The topographical information may be in the form of, for example, data obtained from a CAD file of the device's design, from a critical dimension (CD) measurement tool, such as CDSEM, OCD, AFM, etc. Data relevant to the calibration may include CD at the top of a feature, CD at the bottom of a feature, height of the features, pitch, etc. According to a feature of the invention, this data may be used to generate one or more calibration coefficients that are then used to normalize the XPS/XRF data. For example, one calibration coefficient may be correlated to the top CD, one calibration coefficient may be correlated to the bottom CD, one calibration coefficient may be correlated to the feature's height, one calibration coefficient may be correlated to the pitch, etc. Depending on the device's design, one or more of these coefficients may be used.

An elemental species refers to the chemical composition of a specific layer or the substrate. For example, a hafnium oxide layer includes the elemental species of hafnium and oxygen. Another example would be a SiGe layer that includes the elemental species of Si and Ge. An electron/x-ray species refers to an electron/x-ray having a characteristic energy. A single elemental species may emit several different electron species. For example, a silicon substrate may emit two different characteristic electrons having different kinetic energies. One electron may be emitted from the 2p orbital of the silicon atom, while the other electron may be emitted from the 2s shell of the silicon atom. An electron signal hereinafter refers to a stream of electrons belonging to a specific electron species. For example, the 'Hf4f signal' comprises the electrons emitted by the 4f orbital of hafnium. Another example would be the 'GeLα signal' which comprises x-rays from the Lα x-ray emission from Ge. Many of the examples discussed below refer to photoelectrons, or electrons that are emitted when a layer is bombarded with photons. Each elemental species may emit one or more photoelectron/x-ray species, which may comprise a photoelectron/x-ray signal.

Figure 1B:
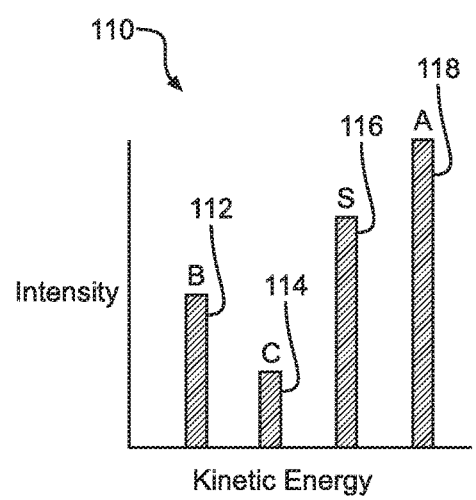
Figure 1C:
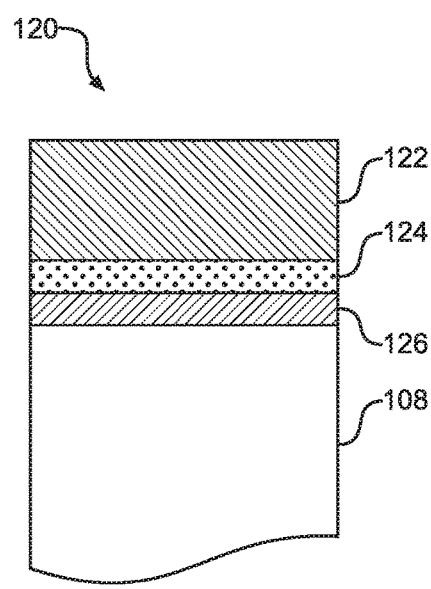
Figure 1D:
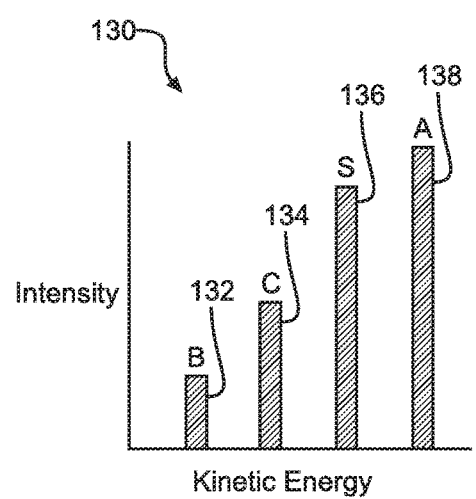

FIGS. 1A-1D illustrate two multi-layer structures and the intensities of different electron signals emitted by the structures when subjected to photoelectron spectroscopy. FIG. 1A illustrates a multi-layer structure 100 having three layers 102, 104, and 106 formed on a substrate 108. Each of the layers 102, 104, and 106, and the substrate 108, emit electrons having a characteristic kinetic energy (KE) when bombarded with energetic particles, such as photons or electrons. FIG. 1B is a graph 110 showing the intensity of an electron species emitted by each layer of the structure 100. FIG. 1C illustrates a multi-layer structure 120 having three layers 122, 124, and 126 formed on a substrate 128. FIG. 1D is a graph 130 showing the intensity of an electron species emitted by each layer of the substrate 120.

In embodiments disclosed in more details below the thickness or composition of a layer in a structure may be determined by generating a ratio of two predictive intensity functions of electron signals. As will be explained below, the predictive intensity functions are dependent on the thickness of the layer that produces the electron. A ratio of two predictive intensity functions is used to allow for variances in the intensity of the beam used to generate the electrons, and other factors that may change the relative intensities of electron or x-ray signals. Once the ratio including the predictive intensity functions for the emitted electrons is determined, the measured intensities of those electron signals is inputted, and using iteration or other techniques, the thickness of a layer can be determined. Various examples below describe different scenarios for determining thicknesses and/or composition.

Photoelectron spectroscopy is a technique used to determine the composition and electronic state of a sample. Photoelectron spectroscopy measures photoelectrons that are emitted by a sample that has been bombarded by essentially monochromatic (or of narrow line width) sources of radiation. For example, the sample may be bombarded with x-ray or ultraviolet radiation having a specific, predetermined wavelength. When the individual atoms of the sample absorb the photons of the radiation, the atoms emit an electron having a kinetic energy (KE) characteristic of the atom. This electron is known as a photoelectron. The photon absorbed by the atom has an energy e=hv. The photoelectron is an electron that was once bound to the emitting atom. The binding energy (BE) of the photoelectron is the amount of energy required to strip the photoelectron from the atom. The KE measured by the equipment is the amount of energy the photoelectron has after being emitted. Because of the law of conservation of energy, it can be determined that KE=hv−BE. As the BE for an electron in an atom has a known value, if the wavelength of the photon striking the sample is known, the KE of an emitted photoelectron can identify the species of the photoelectron.

Auger electron spectroscopy exposes a sample to a beam of electrons having sufficient energy to ionize atoms, thereby causing an atom to emit an Auger electron. When an atom is exposed to the beam, a first electron is removed from a core level of the atom, creating a vacancy. An electron from a higher level of the atom fills the vacancy, causing a release of energy. The released energy is carried off with an ejected Auger electron. The Auger electron, and the intensity of an Auger electron signal can be measured in the same way that the photoelectron signal is measured. It is understood that wherever photoelectrons are mentioned herein, Auger electron species may also be measured and used to determine thicknesses. Additionally, other electron species that have a characteristic energy and whose intensities may be measured may also be used with embodiments of the invention.

The emitted photoelectrons can be counted using an electron energy analyzer. A spectrum plotting the number of photoelectrons counted at specific kinetic energies can be generated from the raw data. The spectrum can then be used to determine various characteristics, such as the composition or the thickness, of the sample. According to one embodiment of the invention, constant-angle (e.g., the x-ray source remains at a constant angle) spectroscopy is used to determine layer thickness.

X-ray photoelectron spectroscopy (XPS) is photoelectron spectroscopy using an x-ray source. Using XPS or similar techniques, one may determine the thickness of the layers 102, 104, 106, 122, 124, or 126. In order to determine the thickness of the layer 102, the structure 100 is bombarded with x-ray wavelength photons from an x-ray source to stimulate the emission of a characteristic photoelectron using the photoelectric effect. When a photon having a specific wavelength is absorbed by an atom in a molecule or solid, a core (inner shell) electron having a specific, characteristic energy for that species is emitted. The kinetic energy of the emitted photoelectrons can be used to determine the thickness and other characteristics of the layer that generated them.

The various layers of the structures 100 and 120 each have corresponding elemental species. For example, the layer 102 and the layer 122 have the same elemental species, the layer 104 and the layer 124 have the same elemental species, and the layer 106 and the layer 126 have the same elemental species. Since the elemental species of the layers 102 and 122 is the same, the layers 102 and 122 will emit photoelectrons having the same characteristic KE. The two structures 100 and 120 are identical except for the thickness of the middle layers of each (i.e., the layers 104 and 124). While the layers 102 and 122 have the same thickness, and the layers 106 and 126 have the same thickness, the layer 104 is thicker than the layer 124. This is significant since the intensity of photoelectrons emitted by buried layers is attenuated by the layers above them.

As shown in FIGS. 1B and 1D, the intensity 112 of the photoelectron signal emitted by the layer 104 is greater than the intensity 132 of photoelectron signal emitted by the layer 124. All of the photoelectrons emitted by the layers 104 and 124 have the same kinetic energy, however, the thicker layer 104 emits more photoelectrons (i.e., has a higher intensity), which indicates that the layer 104 is thicker than the layer 124. Since a predictive intensity function that is dependent on the thickness of the layer can be formulated for each photoelectron species, the measured intensity of the photoelectrons can be used to determine the thickness of the various layers of the structures 100 and 120.

As can be seen in FIGS. 1B and 1D, the intensities 118 and 138 of the signals emitted by the layers 102 and 122 are the same. This is because the layers 118 and 138 have the same thickness, and because the signals emitted by the layers 118 and 138 are not attenuated by an overlayer. The intensity 136 of the signal emitted by the substrate 128 is greater than the intensity 116 of the signal emitted by the substrate 108. This is because the signal emitted by the substrate 108 is more attenuated than the signal emitted by the substrate 128. The substrates 108 and 128 are considered to be infinitely thick (i.e., they have a thickness greater than four times the wavelength of the incoming photons) and will therefore produce approximately the same number of characteristic photoelectrons under the same conditions. The thicker layer 104 attenuates the signal emitted by the substrate 108 more than the thinner layer 124 attenuates the signal emitted by the substrate 128. For the same reason, even though the layers 106 and 126 have the same thickness, the intensity 114 of the signal emitted by the layer 106 is less than the intensity 134 of the signal emitted by the layer 126. The intensity 112 of the signal emitted by the layer 104 is greater than the intensity 132 of the signal emitted by the layer 124 since the layer 104 is thicker than the layer 124, and a thicker layer emits more photoelectrons.

Figure 2A:
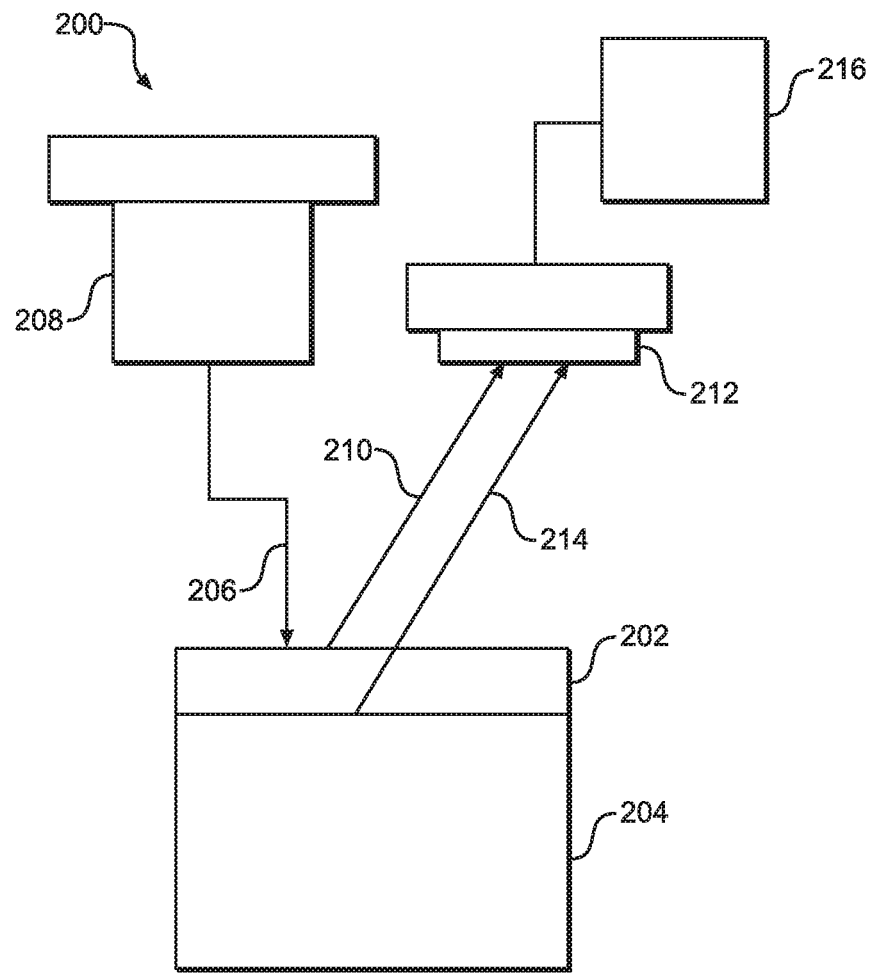
FIG. 2A illustrates a layered structure formed on a substrate according to one embodiment of the invention.
Figure 2B:
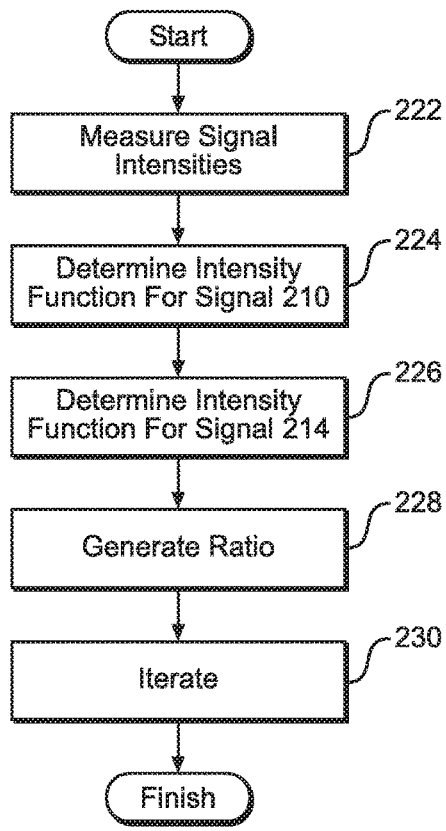
FIG. 2B is a flowchart describing a process for determining a thickness and/or composition of a single layer over a substrate.
Figure 2C:
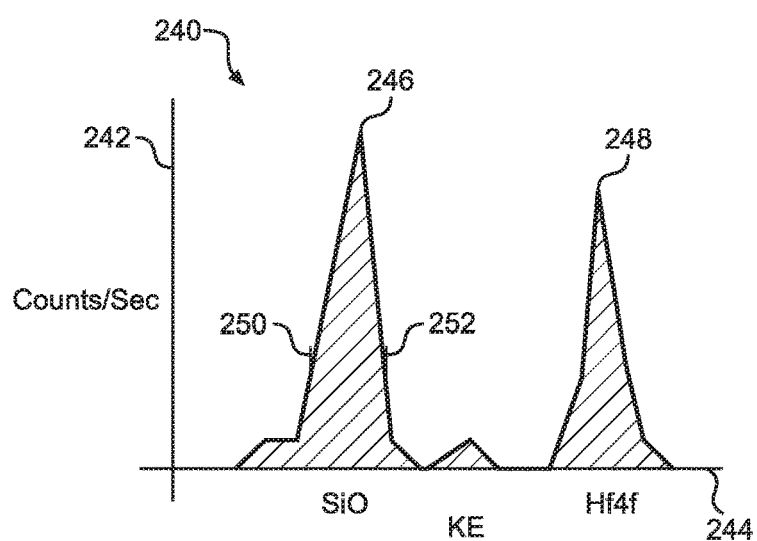
FIG. 2C illustrates a spectrum of the measured results generated by XPS spectroscopy.

FIGS. 2A-C describe a process for determining a thickness of a single layer over a substrate using an electron signal from the layer and an electron signal from the substrate. FIG. 2A illustrates a layered structure formed on a substrate and investigated according to one embodiment of the invention. For simplicity of explanation, in this example there is only one thin layer deposited over the substrate, but the way to generalize the method for more layers will be described further below. The discussion regarding FIG. 2A provides a general formulation of a ratio used to determine a thickness of a single flat layer, i.e., without any topographical structures. FIG. 2A shows a structure 200 including a layer 202 formed on a silicon or other substrate 204 which may represent a portion of a larger micro-electronic device. The thickness of the layer 202 may be measured using X-Ray Photoelectron Spectroscopy (XPS) or similar techniques, such as Ultraviolet Photoelectron Spectroscopy (UPS), Auger spectroscopy, etc.

FIG. 2B is a flowchart describing a process for determining a thickness of a single layer over a substrate. The process illustrated in FIG. 2B may be executed by a module, which may be implemented in hardware, software, or a combination of hardware and software. As such, the process of FIG. 2B may be implemented as a machine readable medium having stored thereon executable program code which, when executed, causes a machine to perform a method of FIG. 2B. The module or machine readable medium may reside in a computer independent of the metrology tool, or may be part of a CD, XPS, or other metrology tools.

The process 220 uses two electron signals (one from the layer 202 and one from the substrate 204) to determine the thickness of the layer 202. The intensities of the two electron signals are first measured. Predictive intensity functions dependent on the thickness of the layer 202 are determined. A ratio of the two functions (one predicting the intensity of the signal from the layer 202, the other predicting the intensity of the signal from the substrate 204) is generated, and the thickness of the layer 202 is extracted from the ratio. This will be explained in more detail below.

Referring back to FIG. 2A, the structure 200 includes the substrate 204 that forms the basis for the structure 200 and may be formed from, e.g., single-crystal silicon. The layer 202 is formed over the substrate 204. The layer 202 in this example may be, e.g., a Hafnium Oxide ($HfO_2$) layer. Although specific examples of layer species are used herein, it is understood that any layer material may be used with embodiments of this invention.

Generally, the thickness of the layer 202 can be determined by taking a ratio of the intensities of two measured signals of photoelectrons emitted by the layer 202 and the substrate 204. A hafnium atom, when bombarded with x-ray wavelength photons 206 generated by an x-ray source 208, emits a characteristics photoelectron signal 210 comprising photoelectrons (for example) from the 4f orbital. The x-ray source 208 may include, for example, an electron gun to direct electrons at an anode to generate x-ray photons, and a lens to focus the x-ray photons on the structure 200. The photoelectrons comprising the signal 210 have a characteristic kinetic energy that is measured and counted by an electron energy analyzer 212. The substrate 202 also emits a characteristic signal 214 comprising photoelectrons emitted by the Si2p shell and influenced by the Si—Si bond (the "SiO" photoelectron). The signal 214 is also measured by the analyzer 212. One or both of the signals 210 or 214 may also comprise Auger electrons or other ejected characteristic energy electrons. For example, the signal 210 may be an Auger electron signal, while the signal 214 is the SiO photoelectron signal.

The analyzer 212 returns the measured results to a processing system 216. The processing system 216 may be a personal computer (PC) such as those having Intel® processors, and may interface with the analyzer 212 through a universal serial bus (USB) connection. The measured results are processed by the processing system 216 and returned to a user.

FIG. 2C illustrates a spectrum 240 of the measured results generated by XPS spectroscopy. The spectrum 240 shows a number of counts per second measured along the y-axis 242, and a kinetic energy (KE) of the measured-photoelectrons along the x-axis 244. The spectrum 240 shows two peaks, 246 and 248, corresponding to the measured signals 212 and 210, respectively. The number of counts as shown in the peaks 246 and 248 is used to determine the intensity of the signals 210 and 212. The peak 246 may have a lower bound 250 and an upper bound 252. The number of counts falling between these bounds determine the intensity of the SiO species (i.e., more counts equals higher intensity), which is then used to determine the thickness of the layer 202. The peaks 246 and 248 may also be manipulated (e.g., shaped or fitted) or have background noise removed using standard techniques such as background subtractions.

The intensities of photoelectrons characteristic to a layer (e.g., the layer 202) can be predicted using formulae that depend on the layer thickness and the attenuation of the signals in a film for a given electron analyzer geometry, x-ray source to analyzer angle, operating condition, and x-ray flux of given energy. The process 220 shown in FIG. 2B described determining layer thickness using an electron species from the layer 202 and an electron species from the substrate 204. In block 222, the intensities of the two electron signals 210 and 214 are measured using the analyzer 212 shown above. In block 224, a predictive intensity function for the signal 210 is determined. Equation (1) can be used to determine the intensity of a signal that is not attenuated (i.e., a signal emitted by the top layer of a structure):

$$I(X_i) = I_{infXi} * \left[1 - e^{\frac{-tx}{\lambda Xi(X)}}\right] \quad (1)$$

Where X is an elemental species, $X_i$ is the photoelectron species emitted by the species X which is being measured, $I(X_i)$ is the intensity of the photoelectron signal, $I_{infXi}$ is the intensity of a photoelectron signal emitted by a thick layer (i.e., greater than 10 nanometers (nm) or having thickness at least four times larger than the photoelectron species wavelength), $t_x$ is the thickness of the layer emitting the signal, and $\lambda_{Xi(X)}$ is the electron attenuation length (EAL) of the photoelectron species ($X_i$) in a layer X. An EAL is a measured quantity equal to the distance over which a photoelectron's original intensity drops to 1/e. EALs may be determined using, for example, the National Institute of Science and Technology's (NIST) EAL program. For example, the intensity of the signal 210 emitted by the layer 202 can be predicted using equation (1), wherein the predicted intensity of the photoelectron signal equals the intensity of a photoelectron signal emitted by a thick layer, multiplied by a factor having a magnitude dependent on a ratio of the thickness of the layer to the electron attenuation length (EAL) of the photoelectron species in that layer.

In block 224, a predictive intensity function for the signal 214 is determined. The intensity of the signal 214 emitted by the substrate (or underlayer) 204 of thickness $t_x$ is attenuated by the layer 202, and therefore may be predicted using equation (2):

$$I(X) = I_{infX} * \left[1 - e^{\left(\frac{-t_x}{\lambda X(X)}\right)}\right] * e^{\frac{-t_y}{\lambda X(Y)}} \quad (2)$$

Where $I(X)$ is the intensity of a photoelectron signal comprising a photoelectron species X and attenuated by an overlayer Y of thickness $t_y$, $\lambda_{X(Y)}$ is the EAL of photoelectrons species X attenuated by layer y, and $\lambda_{X(X)}$ is the EAL of photoelectrons species X attenuated by layer x. That is, the predicted intensity of the photoelectron signal from the layer equals the intensity of a photoelectron signal emitted by a thick layer (e.g., substrate), multiplied by a factor having a magnitude dependent on a ratio of the thickness of the layer to the electron attenuation length (EAL) of the photoelectron species in that layer, and further multiplied by a factor having a magnitude dependent on the ratio of the thickness of the overlayer to the EAL of photoelectrons X emitted from layer x attenuated by the overlayer y. In the limit of a very thick layer or substrate, for which tx is very large, the second term in the equation approaches 1, and thus can be omitted from the equation.

In order to determine the thickness of the layer 202, the ratio of the intensities of the two signals 210 and 214 is determined in block 228. A ratio is used because the specific intensities measured by the analyzer 212 change from measurement to measurement and depend on the x-ray wavelength used and other factors. The ratio of the intensities of the signals 210 and 214 for the example of layers with elemental Hafnium, oxide and Silicon substrate (or thick layer) may be given, for example, by equation (3):

$$\frac{I(SiO)}{I(Hf4f)} = \frac{I_{infSi} * e^{\frac{-t_{Hf}}{\lambda_{Si(HfO2)}}}}{I_{infHf} * \left(1 - e^{\frac{-t_{Hf}}{\lambda_{Hf(HfO2)}}}\right)} \quad (3)$$

Equation (3) may be solved iteratively to determine the thickness $t_{Hf}$ using a program such as Matlab® in block 230. I(Hf4f) is the measured intensity of photoelectrons emitted by the 4f shell of hafnium (i.e., the signal 210 and the peak 228), while I(SiO) is the measured intensity of photoelectrons emitted by the substrate 202. $I_{(infHf)}$ and $I_{(infSi)}$ are the measured intensities of a photoelectron emitted by a thick (e.g., greater than 10 nm) layer of hafnium oxide and silicon, respectively. $\lambda_{Si(HfO2)}$ and $\lambda_{Hf(HfO2)}$ are the measured electron attenuation lengths (EALs) of silicon and hafnium photoelectrons emitted by the substrate 204 and the layer 202. The intensity of the silicon signal 214 is attenuated by the layer 204.

Note that in this example, since the substrate is thick, the second term from equation (2) has been omitted. Consequently, the ratio of the measured intensity of photoelectrons emitted by element $x_i$ in the substrate to the measured intensity of photoelectrons emitted by element $x_j$ in the overlayer equals the ratio of the measured intensities of a photoelectron emitted by element $x_i$ in a thick layer as modified by a first factor, to the measured intensities of a photoelectron emitted by element $x_j$ in a thick layer as modified by a second factor, wherein the first factor correlates with a ratio of the thickness of the overlayer to the EALs of element $x_i$ in the overlayer; while the second factor correlates with a ratio of the thickness of the overlayer to the EALs of element $x_j$ in the overlayer.

So far, the process has been described without regards to the topography of the sample. In essence, the model assumes a flat topography. However, XPS measurements are increasingly important for the fabrication of electronic devices, where the area measured is not flat, but rather has varied or undulated topography. Generalizing, the topography has hills and valleys with repetitive pitch. In one example, such topography may be modeled and referred to as trapezoidal fin structure, as shown in FIG. 3. In the example of FIG. 3, a bulk layer, e.g., mono-silicon substrate 300 is covered with trapezoidal structures, only two of which 305 and 310 are shown for demonstration. The entire surface is covered with a first thin layer 315, e.g., hafnium oxide, and a second thin layer 320, e.g., silicon oxide. The objective is to determine the thickness and composition of each of the thin layers. However, attempting to use XPS in the standard method would lead to error, since the photon emission from different parts of the trapezoids is different from emission from a flat surface.

In order to properly account for the varying photon emission, the topography is characterized by several parameters, such as, e.g., fin height, width of each fin at the top (top critical dimension—TCD), width of each fin at the bottom (bottom critical dimension—BCD), side length—a function (L), and pitch (which is the repetition length of the fins). Thus, as shown in FIG. 3, the intensity contribution of a repetitive structure (e.g., fin) is composed of the intensity contribution from the top of the structure, twice the contribution from the sloping sides (there are two sides), and the contribution from the bottom.

In one embodiment, the topography parameters are used to generate coefficients which are used to calibrate the XPS model. In one particular example three coefficients are used: top coefficient, sidewall coefficient, and bottom coefficient. Also, a pitch coefficient may be used. FIGS. 4A and 4B illustrate an embodiment for generating the coefficients, in this example for hafnium, silicon oxide, and silicon, per the example of FIG. 3, while FIG. 4C illustrates another example. In FIG. 4B the "a" and "b" parameters are the relative production and collection efficiency of the photoelectrons for the side of the fins and the bottom, respectively. According to one embodiment, the "a" and "b" parameters need to be calibrated using reference data with known structure parameters.

The $1/K_X$ factors shown in FIG. 4A are essentially the $I_{infX}$ factors presented previously, in all cases representing the effective relative signal strength for photoelectron production of species X for the planar equivalent case.

As shown in FIG. 4B, the structure constants $G_{Top}$, $G_{Sidewall}$, $G_{Bottom}$ are the critical signal intensity scaling factors that encode the relative strengths of the signals as they relate to the geometry of the fins compared to a nominal planar film. For example, $G_{Top}$=p/TCD where p is the pitch of the periodic structure, and TCD is the top width of the fin (also referred to as top critical dimension). Thus, the signal emitted from the top of the fin is a fraction of a nominal planar film in proportion to p/TCD. In the limiting case where TCD=0, $G_{Top}$ approaches infinity and the effective signal from the top of the fin goes to zero. When p=TCD, $G_{Top}$=1, reducing to the planar film equivalent signal contribution.

Similarly, for $G_{Bottom}$ the fraction of signal emitted from the bottom region of the fin is of fraction p/(p-BCD) relative to the nominal planar film case, multiplies by calibration parameter b. The limiting cases where p=BCD and $G_{Bottom}$ approaches infinity (no signal from the bottom region) and BCD=0 and $G_{Bottom}$=1 (planar equivalent) is evident.

Finally, for $G_{Sidewall}$ the fraction of signal emitted from the side region of the fin scales with the effective length of the sidewall which is in turn related to the difference between the top (TCD) and bottom (BCD) widths of the fin and the height h of the fin. This is modified by calibration parameter a. The limiting cases where p=BCD and $G_{Bottom}$ approaches infinity (no signal from the bottom region) and BCD=0 and $G_{Bottom}$=1 (planar equivalent) is evident.

The final signal contribution for each species shown in FIG. 4A is therefore a sum of the individual signals coming from the three different regions of the fin and their respective contributions each scaled by their respective constants $G_{Top}$, $G_{Sidewall}$, $G_{Bottom}$.

As also shown in FIG. 4B, when the aspect ratio of the fins is low, i.e., the height of the sides of the fins is small compared with the width of the bottom of the fins, the calibration parameter b is approximately equal to 1, so that it may be dropped and only calibration parameter a used. This is because the contribution of the wide bottom can be approximated by a flat surface; however the contribution of the sides needs to be calibrated by calibration parameter a. FIG. 4B also indicates the constraints that the pitch is larger than the bottom CD—which is the case for any repetitive structure by definition. Also, the top CD is taken to equal or be smaller than the bottom CD. Parameter b is set to one when the height h, shown in FIG. 3, is much smaller than the bottom CD and the pitch p.

An alternative model is also presented in FIG. 4C, that leads to slightly different relationships for the $G_{Top}$, $G_{Sidewall}$, $G_{Bottom}$ factors. In the case where the finite thickness of the films need to be considered for improved accuracy of the model, the $G_{Top}$, $G_{Sidewall}$, $G_{Bottom}$ factors now contain an explicit thin film dependence and the model may use four calibration parameters. In the examples of FIGS. 4A-4C, the calibration parameters a-d may be different for each photoelectron species.

Figure 5:
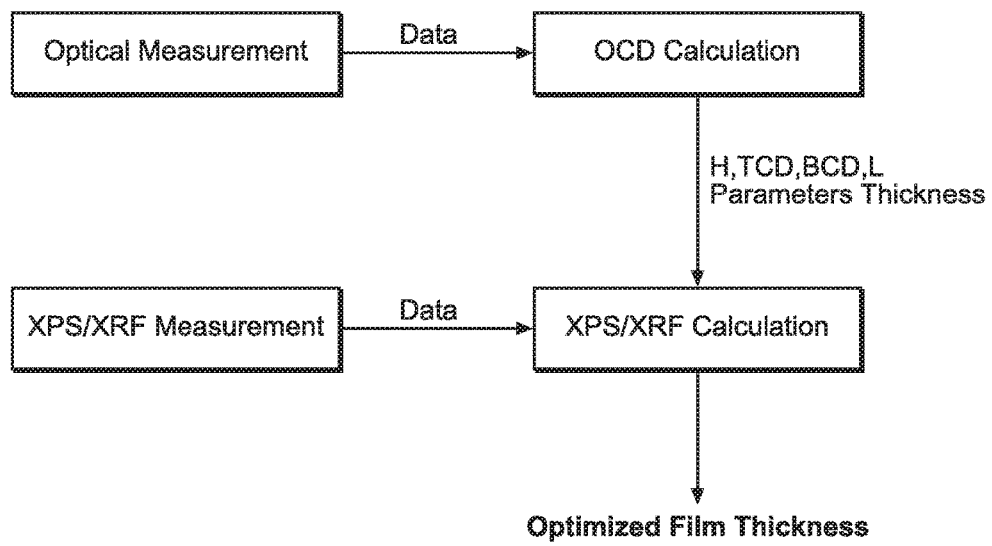
FIG. 5 is a flowchart describing a process for determining a thickness and/or composition of two of the layers of the uneven structure using the coefficients.

The parameters of the sample can be obtained in many ways; either derived from design data or measured using metrology equipment. As shown in FIG. 5, according to one example, the parameters are obtained using optical measurement of the sample, e.g., optical CD tool, such as the Nova T600, available from Nova Measuring Instruments of Rehovot, Israel.

The process illustrated in FIG. 5 may be executed by a module, which may be implemented in hardware, software, or a combination of hardware and software. As such, the process of FIG. 5 may be implemented as a machine readable medium having stored thereon executable program code which, when executed, causes a machine to perform a method of FIG. 5. The module or machine readable medium may reside in a computer independent of the metrology tool, or may be part of a CD, XPS, or other metrology tools. Also, in FIG. 5, the double-headed arrow indicates processes that may be performed iteratively.

In another embodiment, the topography may be non-periodic (consistent with real device layout where an XPS measurement might take place). Such topography can be derived or measured from CAD, GDS II layout, and/or material and thickness information for different layers measured at the current or previous steps of the process. Such non-periodic topography may also be characterized by a "top", "side" and "bottom" production of electrons, or other, more complex combination of coefficients depending on the layout complexity. The relative electron contribution of different aspects of the structure can then be similarly summed up to account for the electron signals collected and enable correct measurement of the thin layers around that structure.

In yet another embodiment, concurrent or iterative spectrum interpretation and optimization is performed on the OCD spectra (to extract the geometrical profile including topography of the structure and thin film layers) and XPS signals that use the topography to refine extraction of thin film layers covering partially or fully the topography. The topography extracted from OCD (consistent with measured spectra) would constrain the XPS interpretation to a specific result for the thin layer thickness and/or composition, which in turn would put further constraints on the OCD-extracted topography. This method further minimizes possible crosstalk errors between geometrical profile parameters (topography and thin films).

Figure 6:
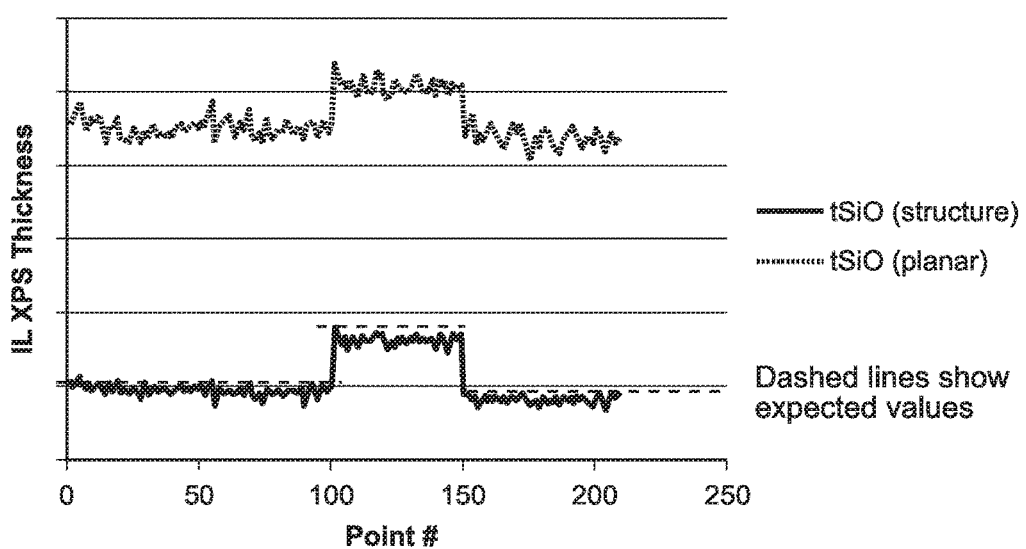
FIG. 6 is a plot of data obtained using embodiments of the invention, with and without the use of the coefficients.

FIG. 6 is a plot of data obtained using embodiments of the invention. The top plot illustrates plot of the data calculation obtained without using topography parameter coefficients, i.e., using the modeling of flat surface, while the bottom is a plot of the data calculation using the topography parameter coefficients to improve on the results of the top plot. The horizontal dashed lines indicates the expected value from knowledge of the actual structure. It can be seen that using the parameters dramatically improves on the data calculation.

It should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein.

The present invention has been described in relation to particular examples, which are intended in all respects to be illustrative rather than restrictive. Those skilled in the art will appreciate that many different combinations of hardware, software, and firmware will be suitable for practicing the present invention. Moreover, other implementations of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for determining a property of a layer of an integrated circuit (IC), the layer being formed over an underlayer, comprising the steps of:
   irradiating the IC to thereby generate emission from the IC;
   collecting the emission from the IC and determining the kinetic energy of emitted species within the emission to thereby calculate emission intensity of various species emitted from the layer and emission intensity of species emitted from the underlayer;
   calculating a ratio of the emission intensity of species emitted from the layer and emission intensity of species emitted from the underlayer;
   using the ratio to determine material composition or thickness of the layer;
   wherein topography of the IC is modeled as having repetitive fin structure, and the intensity of each element is calculated using emission contribution from a top surface of the fin, twice emission contribution from a sidewall of the fin, and emission contribution from a bottom part of the fin.

2. The method of claim 1, wherein the steps of irradiating IC and collecting emission is performed using one of x-ray photoelectron spectroscopy (XPS) or x-ray fluorescence spectroscopy (XRF).

3. The method of claim 1, wherein a predictive intensity function that is dependent on the thickness of a layer is determined for each emission species and a ratio of two predictive intensity functions is formulated; and wherein the ratio is iterated to improve the determined thickness of the layer.

4. The method of claim 1, wherein the intensity of electrons emitted from the layer is calculated by multiplying an intensity of a photoelectron signal emitted by a theoretically infinitely thick layer, multiplied by a factor having a magnitude dependent on a ratio of the thickness of the layer to the electron attenuation length (EAL) of the photoelectron species in the layer.

5. The method of claim 1, wherein the intensity of electrons emitted from the layer is calculated using the relationship:

$$I(X_i) = I_{inf}X_i * \left[1 - e^{\frac{-tx}{XXi(X)}}\right]$$

Where X is an elemental species X in the layer, $X_i$ is photoelectron species emitted by the species X which is being measured, I(X$_j$) is intensity of the photoelectron signal, I$_{infXi}$ is an intensity of a photoelectron signal emitted by the underlayer, t$_x$ is thickness of the layer, and λ$_{Xi(X)}$ is electron attenuation length (EAL) of the photoelectron species (X$_i$) in the layer.

6. The method of claim 4, wherein the intensity of electrons emitted from the underlayer is calculated by multiplying an intensity of photoelectron signal emitted by a theoretically infinitely thick layer by a first factor having a magnitude dependent on a ratio of thickness of the under layer to the electron attenuation length (EAL) of the photoelectron species in the underlayer, and further multiplied by a second factor having a magnitude dependent on a ratio of thickness of the layer to an EAL of photoelectrons attenuated by the layer.

7. The method of claim 5, wherein the intensity of electrons emitted from the underlayer is calculated using the relationship:

$$I(X) = I_{infX} * e^{\frac{-ty}{\lambda X(Y)}}$$

Where I(X) is the intensity of a photoelectron signal comprising a photoelectron species X, t$_y$ is the thickness of the layer, λ$_{X(Y)}$ is the EAL of photoelectrons emitted by the species X in the layer, and λ$_{X(X)}$ is the EAL of photoelectrons emitted by the species X in the underlayer.

8. The method of claim 1, wherein the ratio is calculated by using the relationship:

$$\frac{I(L)}{I(U)} = \frac{I_{infXi} * e^{\frac{-t_{Xj}}{\lambda Xi(L)}}}{I_{infXi} * \left(1 - e^{\frac{-t_{Xj}}{\lambda Xj(L)}}\right)}$$

wherein I(L) is measured intensity of photoelectrons emitted by the layer, while I(U) is measured intensity of photoelectrons emitted by the underlayer, I(infXi) and I(infXj) are measured intensities of a photoelectron emitted by a greater than 10 nm layer of Xi element and Xj element, respectively, λXi(L) and λXj(L) are measured electron attenuation lengths (EALs) of elements Xi and Xj photoelectrons emitted by the underlayer and the layer.

9. The method of claim 1, wherein the ratio is calculated by measured intensities of a photoelectron emitted by element x$_i$ in a theoretically infinitely thick layer as modified by a first factor, to the measured intensities of a photoelectron emitted by element x$_j$ in a theoretically infinitely thick layer as modified by a second factor, wherein the first factor correlates with a ratio of a thickness of the layer to EALs of element x$_i$ in the layer; and the second factor correlates with a ratio of a thickness of the layer to the EALs of element x$_j$ in the layer.

10. The method of claim 1, wherein each emission contribution is modified by a coefficient and wherein the coefficient correlates to a pitch of the repetitive fin structure, the width of the top surface, the width of the bottom part, and height of the fin structure.

11. A metrology module for determining a property of a layer of an integrated circuit (IC), the module comprising:
a first input port coupled to an optical CD tool and configured for receiving parameters corresponding to topography of a top surface of the IC;
a second input port configured for receiving radiation intensity signal corresponding to radiation obtained from the top surface of the IC;
a coefficient generator receiving the parameters and calculating at least one coefficient therefrom;
a calibration module receiving the coefficient and using the coefficient to calibrate the radiation intensity signal to thereby produce a calibrated signal;
a determination module receiving the calibration signal and using the calibration signal to generate a determination of the property of the layer.

12. The metrology module of claim 11, wherein the second input port is coupled to a sensor of an x-ray photoelectron spectroscopy (XPS).

13. The method of claim 12, wherein the second input port is coupled to a sensor of an x-ray fluorescence spectroscopy (XRF).

14. The metrology module of claim 11, wherein the property comprises at least one of thickness and chemical composition.

15. A metrology module for determining a property of a layer of an integrated circuit (IC), the module comprising:
a first input port configured for receiving parameters corresponding to topography of a top surface of the IC;
a second input port configured for receiving radiation intensity signal corresponding to radiation obtained from the top surface of the IC;
a coefficient generator receiving the parameters and calculating at least one coefficient therefrom;
a calibration module receiving the coefficient and using the coefficient to calibrate the radiation intensity signal to thereby produce a calibrated signal;
a determination module receiving the calibration signal and using the calibration signal to generate a determination of the property of the layer; and,
wherein the parameters comprise at least one of: width of upper surface of a feature on the top surface of the IC, width of bottom surface of a feature on the top surface of the IC, height of a feature on the top surface of the IC, length of sidewall of a feature on the top surface of the IC, pitch of multiple features on the top surface of the IC.

16. The metrology module of claim 15, wherein the coefficients comprise a top coefficient correlated to the width of upper surface of a feature on the top surface of the IC, a sidewall coefficient correlated to length of sidewall of the feature on the top surface of the IC, and bottom coefficient correlated to width of bottom surface of the feature on the top surface of the IC.

17. A metrology module of claim 15, wherein the top coefficient, the sidewall coefficient and the bottom coefficient further correlate to a pitch of multiple features on the top surface of the IC.

18. A system for determining a thickness of a layer in a multi-layer structure, comprising:
a critical dimension metrology tool;
a thickness measurement metrology tool;
a thickness determining module, comprising:
a first input port coupled to the critical dimension metrology tool and configured for receiving from the critical dimension metrology tool parameters corresponding to topography of a top surface of the IC;
a second input port configured for receiving radiation intensity signal from a sensor of the thickness measurement metrology tool, the radiation intensity signal corresponding to radiation detected by the sensor from the top surface of the IC;

a coefficient generator receiving the parameters and calculating at least one coefficient therefrom;
a calibration module receiving the coefficient and using the coefficient to calibrate the radiation intensity signal to thereby produce a calibrated signal;
a determination module receiving the calibration signal and using the calibration signal to generate a determination of the thickness of the layer.

* * * * *